(12) United States Patent
Choi et al.

(10) Patent No.: US 7,968,013 B2
(45) Date of Patent: Jun. 28, 2011

(54) CARBON NANOTUBE N-DOPING MATERIAL, CARBON NANOTUBE N-DOPING METHOD AND DEVICE USING THE SAME

(75) Inventors: Jaeyoung Choi, Yongin-si (KR); Hyeon Jin Shin, Yongin-si (KR); Seonmi Yoon, Yongin-si (KR); Boram Kang, Yongin-si (KR); Young Hee Lee, Yongin-si (KR); Un Jeong Kim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 261 days.

(21) Appl. No.: 12/350,558

(22) Filed: Jan. 8, 2009

(65) Prior Publication Data

US 2010/0140561 A1 Jun. 10, 2010

(30) Foreign Application Priority Data

Jun. 5, 2008 (KR) .................. 10-2008-0053349

(51) Int. Cl.
*H01B 1/00* (2006.01)
*H01L 29/08* (2006.01)
*D01F 9/00* (2006.01)

(52) U.S. Cl. ........ 252/511; 252/500; 252/502; 252/510; 423/447.1; 423/447.2; 423/447.3; 257/40; 257/E51.001; 438/584; 977/742; 977/745; 977/746; 977/788; 977/795

(58) Field of Classification Search .............. 252/500, 252/502, 510, 511; 423/447.1, 447.2, 447.3; 257/40, E51.001; 438/584; 977/742, 745, 977/746, 788, 795
See application file for complete search history.

(56) References Cited

U.S. PATENT DOCUMENTS

| | | | |
|---|---|---|---|
| 2005/0041458 A1* | 2/2005 | Lossau et al. ................ | 365/151 |
| 2007/0278111 A1 | 12/2007 | Boussaad et al. | |
| 2008/0160384 A1* | 7/2008 | Iqbal et al. .................... | 429/34 |
| 2010/0044230 A1* | 2/2010 | Papadimitrakopoulos et al. ........................ | 204/547 |

FOREIGN PATENT DOCUMENTS

KR  10-2006-0073019  6/2006

OTHER PUBLICATIONS

O'Connel et al. "Chiral selectivity in the charge-transfer bleaching of single-walled carbon-nanotube spectra." Nature, vol. 4, pp. 512-418, May 2005.*
Kang et al. "Restorable type conversion of carbn nanotubes transistor using pyrolytically controlled antioxidizing photosynthesis coenzyme." Adv Funct Mat., vol. 29, pp. 2553-2559, Aug. 2009.*
Banks et al. "Exploring the electrocatalytic sites of carbon nanotubes for NADH detection: an edge plane pyrolytic graphite electrode study." Analyst, vol. 130, pp. 1232-1239, Aug. 2005.*
Pumera et al. "A mechanism of adsorption of B-nicotinamide adenine dinucleotide on graphene sheets: experiment and theory." Chem. Eur., vol. 15, pp. 10851-10856, 2009.*
Lawrence et al. Chemical adsorption of phenothiazine dyes onto carbon nanotubes: toward the low potential detection of NADH. Electroc. Comm. vol. 8, pp. 71-76, Nov. 2005.*

* cited by examiner

*Primary Examiner* — Mark Kopec
*Assistant Examiner* — Tri V Nguyen
(74) *Attorney, Agent, or Firm* — Cantor Colburn LLP (57) ABSTRACT

Nicotinamide and/or a compound which is chemically combined with nicotinamide may be used as a carbon nanotube ("CNT") n-doping material. CNTs n-doped with the CNT n-doping material may have long-lasting doping stability in the air without de-doping. Further, CNT n-doping state may be easily controlled when using the CNT n-doping material. The CNT n-doping material and/or CNTs n-doped with the CNT n-doping material may be used for various applications.

20 Claims, 9 Drawing Sheets

CARBON NANOTUBE N-DOPING MATERIAL, CARBON NANOTUBE N-DOPING METHOD AND DEVICE USING THE SAME

This application claims priority to Korean Patent Application No. 10-2008-0053349, filed on Jun. 5, 2008, and all the benefits accruing therefrom under U.S.C. §119, the contents of which in its entirety are herein incorporated by reference.

BACKGROUND

1. Field

This disclosure relates to a carbon nano-tube ("CNT") n-doping material, a CNT n-doping method and a device using the same.

2. Description of the Related Art

CNTs may be used to manufacture a variety of electronic devices including p-n junction diode, field-effect transistor, light-emitting device, complementary metal oxide semiconductors ("CMOS") as well as CNT composites, solar cells, or the like. In order to use CNTs for the purpose, techniques of controlling n-doping and p-doping state may be required.

CNTs may usually have p-doping state right after being prepared. Thus, oxidizing agents which can withdraw electrons from the prepared CNTs may be used for controlling the p-doping state. Examples of oxidizing agents, may include but are not limited to, hydrochloric acid, sulfuric acid, nitric acid, or metal salts examples of which may be but not limited to gold chloride, silver nitrate, etc.

Meanwhile, as for CNT n-doping agents, reducing agents which can donate electrons to CNTs may be used. Examples of the reducing agents may include but are not limited to alkali metals including but not limited to potassium, sodium, etc., or reducing polymers including but not limited to polyethyleneimine ("PEI"), hydrazine, polyaniline, etc.

SUMMARY

Disclosed herein is a novel CNT n-doping material which may maintain a stable n-doping state for a long time without being de-doped. In one exemplary embodiment, nicotinamide and/or a compound which is chemically combined with nicotinamide may be used as the novel CNT n-doping material. In another exemplary embodiment the CNT n-doping material including nicotinamide and/or a compound which is chemically combined with nicotinamide not only may maintain the stable n-doping state for a long time even in the air without being de-doped, but also the n-doping state may be easily controlled when using the CNT n-doping material.

Disclosed herein is a CNT n-doping material wherein the CNT n-doping material may include at least one selected from the group consisting of nicotinamide, a compound which is chemically combined with nicotinamide and any combination thereof.

Disclosed herein is a CNT n-doping method wherein the CNT n-doping method may include: n-doping a CNT with a material comprising at least one selected from the group consisting of nicotinamide, a compound which is chemically combined with nicotinamide and any combination thereof.

Disclosed herein is an n-doped CNT wherein the CNT may be n-doped with a material including at least one selected from the group consisting of nicotinamide, a compound which is chemically combined with nicotinamide and any combination thereof.

Disclosed herein is a device which may include a CNT which may be n-doped with a material including at least one selected from the group consisting of nicotinamide, a compound which is chemically combined with nicotinamide and any combination thereof.

BRIEF DESCRIPTION OF THE DRAWINGS

The above and other aspects, features and advantages of the disclosed embodiments will be more apparent from the following detailed description taken in conjunction with the accompanying drawings in which:

FIG. 7 is an $I_{ds}$-$V_{gs}$ graph showing an n-doping effect when using nicotinamide according to an exemplary embodiment, where the X axis represents $V_{gs}$ (V) and the Y axis represents $I_{ds}$ (A) in FIG. 7a and the X axis represents $V_{gs}$ (V) and the Y axis represents $I_{ds}$ (A) in FIG. 7b;

FIG. 9 is an $I_{ds}$-$V_{gs}$ graph of the p-n junction diode in FIG. 8, where the X axis represents $V_{gs}$ (V) and the Y axis represents $I_{ds}$ (nA) in FIG. 9a and the X axis represents $V_{gs}$ (V) and the Y axis represents $I_{ds}$ (nA) in FIG. 9b;

FIG. 11 is a graph showing the characteristic of the CMOS in FIG. 10, where the X axis represents $V_{gs}$ (V) and the Y axis represents $I_{ds}$ (nA) in FIG. 11a, the X axis represents $V_{gs}$ (V) and the Y axis represents $I_{ds}$ (nA) in FIG. 11b and the X axis represents Vin (V) and the Y axis represents Vout (V) in FIG. 11c.

DETAILED DESCRIPTION

Exemplary embodiments now will be described more fully hereinafter with reference to the accompanying drawings, in which exemplary embodiments are shown. The invention may, however, be embodied in many different forms and should not be construed as limited to the exemplary embodiments set forth herein. Rather, these exemplary embodiments are provided so that this disclosure will be thorough and complete, and will fully convey the scope of the invention to those skilled in the art. In the description, details of well-known features and techniques may be omitted to avoid unnecessarily obscuring the presented exemplary embodiments.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. Furthermore, the use of the terms a, an, etc. do not denote a limitation of quantity, but rather denote the presence of at least one of the referenced item. The use of the terms "first", "second", and the like do not imply any particular order, but are included to identify individual elements. Moreover, the use of the terms first, second, etc. do not denote any order or importance, but rather the terms first, second, etc. are used to distinguished one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements and shape, size and regions, and the like, are exaggerated for clarity.

Nicotinamide and/or a compound which is chemically combined with nicotinamide (hereinafter, "nicotinamide-based compound") may be used as a CNT n-doping material.

Nicotinamide may have the following chemical formula 1.

[Chemical Formula 1]

When nicotinamide is heated, the pyridyl nitrogen may be converted to $N^+$ and an electron may be emitted (see scheme 1 below). This released electron may be involved in CNT n-doping. That is to say, nicotinamide may act as a reducing agent donating an electron to CNT and n-dope CNT.

[Scheme 1]

In one exemplary embodiment, a reduced form of nicotinamide (see chemical formula 2 below) may also be used.

When the reduced nicotinamide is heated, a proton $H^+$ may be released from the benzene ring so that another electron may be emitted in addition to the electron from N in the benzene ring to be converted to $N^+$ (see scheme 2 below). The two electrons may be involved in CNT n-doping.

[Chemical Formula 2]

[Scheme 2]

In addition to nicotinamide, a nicotinamide-based compound, i.e. a compound which is chemically combined with nicotinamide or a reduced form of the nicotinamide-based compound may be used in one exemplary embodiment.

Non-limiting examples of the nicotinamide-based compounds may include nicotinamide mononucleotide ("NMN"), nicotinamide adenine dinucleotide ("NAD"), nicotinamide adenine dinucleotide phosphate ("NADP"), and the like. However, as described above, the nicotinamide-based compound is not limited to these examples, and any compound which may be chemically combined with nicotinamide may be used. As for non-limiting examples, the nicotineamid-based compound may have its molecular weight of about 100,000 or less.

For reference, NMN may have a structure where nicotinamide and one nucleotide may be combined. NAD may have a structure where nicotinamide, two nucleotides and an adenosine ring may be combined. NADP may have a structure where the —OH group (C2' position) of the adenosine ring in NAD may be replaced by phosphate. NMNH may be a reduced form of NMN, and NAD(P)H may be a reduced form of NAD(P). The following chemical formula 3 may show a structural formula of NAD(P)H.

[Chemical Formula 3]

The following Scheme 3 may show an emission of electrons from NAD(P)H by heating.

[Scheme 3]

As seen in Scheme 3, N in the nicotinamide benzene ring of NAD(P)H may be converted to $N^+$ and H bonded to the carbon at the opposite side of the N of the benzene ring may be released to be $H^+$. As a result, two electrons may be emitted and may be involved in CNT n-doping. In the case of NAD (P), one electron may be emitted as N of the nicotinamide benzene ring may be converted to $N^+$.

The reaction mechanism may be similar to that of nicotinamide as shown in Scheme 1 and Scheme 2. The nicotinamide of NAD(P) or NAD(P)H may act as CNT n-doping material. According to experiments described further below, n-doping effect may not be obtained if CNT may be merely n-doped with adenine or other portions of NAD(P)H excluding nicotinamide. This may be the same case for other nicotinamide-based compounds such as NMN, NMNH, and the like.

Nicotinamide of nicotinamide-based compound may contribute to the CNT n-doping due to its participation in oxidation or reduction reaction of the nicotinamide-based compound. Accordingly, for example, an oxidized form NAD $(P)^+$, which may not act any more as the reducing agent to donate electrons, may not be used as the CNT n-doping material.

In an exemplary embodiment, the CNT n-doping method may comprise the following: providing a material comprising at least one selected from the group consisting of nicotinamide and a compound which is chemically combined with nicotinamide to a CNT to be n-doped, and heating the CNT to which the material may be provided. Further, in the CNT n-doping method, the material may be mixed with a solvent to prepare a solution and the solution may be provided to the CNT. As for non-limiting examples, the solvent may be a polar solvent such as water, alcohol, acetone, etc. As well, it is also possible to sublime the material and make the sublimed material contact CNT. The sublimed material may be coated on CNT in an atomic level.

In an exemplary embodiment, the heating condition of the nicotinamide or the nicotinamide-based compound may be determined in view of the CNT n-doping. The CNT n-doping state may be obtained, for example, by controlling the heating condition such as heating temperature and/or the heating time. The heating condition such as the heating temperature and/or heating time may be a variable with which CNT n-doping state may be controlled. The heating temperature may be about 40° C. to about 250° C. When the heating temperature is less than about 40° C., there may be a possibility that the reaction may be slow. Meanwhile, in order to obtain sufficient n-doping, a heating temperature of about 130° C. or more may be used. Further, in order to obtain more sufficient n-doping, a heating temperature of 150° C. or more may be used. At a heating temperature more than about 250° C., there may be possibility that the polymer like nicotinamide or nicotinamide-based compound may be thermally degraded. In view of CNT n-doping, the heating time may be about 10 seconds to 100 hours. In order to obtain sufficient n-doping, a heating time of about 1 minute or more may be used. There may be a possibility that a heating time more than about 60 minutes may reduce a process efficiency. Heating time more than about 100 hours may lead to a reduction of energy efficiency For reference, absorption data and/or I-V data may be used to find the heating temperature and heating time required for the sufficient n-doping. For example, the extent of n-doping under a specific condition may be measured by checking the peak of nicotinamide or nicotinamide-based compound from the absorption data. Also, the extent of n-doping under a specific condition may be measured by analyzing the I-V data.

In an exemplary embodiment, when CNT may be n-doped using nicotinamide and/or nicotinamide-based compound, it is possible to achieve a stable n-doping state without de-doping even in the air, additionally the stable n-doping state may be maintained for a long period of time. Further, since nicotinamide and/or nicotinamide-based compound may not be a metal compound such as alkali metal, there is unlikely to be an oxidation problem which may usually occur when using metal compound as the CNT n-doping material. Accordingly, nicotinamide and/or nicotinamide-based compound may be usefully used as the CNT n-doping material. A compound chemically combined to nicotinamide may be used in view of doping stability due to the fact that the compound further comprises the other portions which may serve as protection layer of the nicotinamide portion, as well as the nicotinamide portion. When the compound chemically combined to nicotinamid is provided to CNT, the nicotinamide portion may contact CNT and lead CNT to be n-doped while the other portions may face the outside of the contact layer so as to protect the nicotinamid portion from air, etc. For example, NAD(P) or NAD(P)H comprise not only nicotinamide but also adenine or other portions. The adenine or other portions serve as a layer protecting nicotinamide and, thus, may inhibit de-doping and improve the doping stability even though CNT n-doped with NAD(P) or NAD(P)H are exposed to air.

In an exemplary embodiment, the CNT n-doping method, the n-doping state of the CNT may be adjusted by controlling the amount of the material. Where the material is mixed with a solvent to prepare a solution and the solution is provided to the CNT, the n-doping state of the CNT may be adjusted by controlling the amount of the solution or the concentration of the material in the solution. The amount of nicotinamide and/or nicotinamide-based compound may affect the n-doping state of CNT. That is, the CNT n-doping state may progress to a greater extent as a larger amount of nicotinamide and/or nicotinamide-based compound is used. The doping state therefore may be adjusted by controlling the amount of nicotinamide and/or nicotinamide-based compound.

In an exemplary embodiment, examples of controlling the amount of nicotinamide and/or nicotinamide-based compound may be as follows: Nicotinamide and/or nicotinamide-based compound may be dissolved in a solvent to prepare a solution. The amount of the solution may be controlled in order to adjust the amount of nicotinamide and/or nicotinamide-based compound. For example, by changing the total number of drops of the solution introduced to CNT. In the alternative, a concentration of nicotinamide and/or nicotinamide-based compound in the solution may be controlled (e.g., about 1 wt %, about 2 wt %, etc.) in order to adjust the amount of nicotinamide and/or nicotinamide-based compound. Since these methods may be directed to control of the amount of nicotinamide and/or nicotinamide-based compound, it can be said that CNT n-doping state may be conveniently controlled with these methods.

In an exemplary embodiment, the nicotinamide and/or nicotinamide-based compound may be used in various applications requiring CNT n-doping. Examples of such applications may include various devices including but not limited to p-n junction device, CNT field-effect transistor ("CNT-FET"), CMOS, and the like.

The embodiments will now be described in further detail with reference to the following examples. The following examples and experiments are for illustrative purposes only and not intended to limit the scope of the claimed invention.

Experiment 1

Experiment on CNT n-doping Effect by NADH

In order to evaluate the CNT n-doping effect by NADH (β-nicotinamide adenine dinucleotide, reduced dipotassium salt, commercially available at Aldrich Chemical Co. Milwaukee Wis. USA), the following experiment is performed. First, NADH solution is prepared. Water is used as solvent. The concentration of the NADH solution is set as 13.5 mM (1 wt %).

Figure 1:
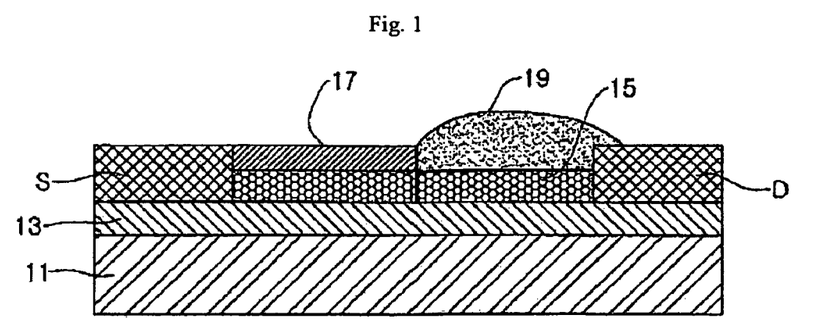
FIG. 1 is a schematic view of carbon nanotube field electric transistor ("CNT-FET") according to an exemplary embodiment.

A CNT field-effect transistor ("CNT-FET") is prepared to evaluate the CNT n-doping effect. FIG. 1 is a schematic view of the prepared CNT-FET.

Referring to FIG. 1, $SiO_2$ insulating layer (13) is formed on $N^+$-doped Si back gate (11), and a source electrode S and a drain electrode D are formed thereon. CNT channel (15) grown by Thermal Chemical Vapor Deposition ("TCVD") is formed between the source electrode S and the drain electrode D.

A photoresist layer (17) is formed on a portion of the CNT channel close to the source electrode S. One drop of the NADH solution (about 100 μL) (19) prepared above is introduced using a micropipette on the remaining portion of the CNT channel close to the drain electrode D, and heated at about 150° C. for about 3 minutes.

Figure 2:
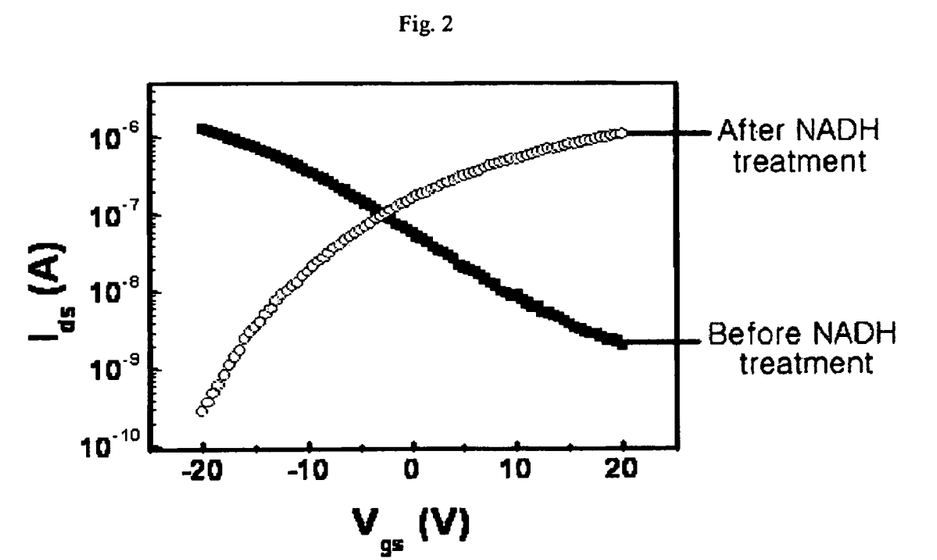
FIG. 2 is an $I_{ds}$-$V_{gs}$ graph showing an n-doping effect when using nicotinamide adenine dinucleotide-H ("NADH") according to an exemplary embodiment, where the X axis represents $V_{gs}$ (V) and the Y axis represents $I_{ds}$ (A)

FIG. 2 is an $I_{ds}$-$V_{gs}$ graph showing an n-doping effect in this experiment.

As seen in FIG. 2, the initial p-doping state of CNT before treating with the NADH solution (In FIG. 2, referred to "before NADH treatment") is changed into n-doping state after treating with the NADH solution (In FIG. 2, referred to "After NAHD treatment").

Experiment 2

Experiment on Change of CNT n-doping State Depending on the Amount of the NADH Solution In order to evaluate the effect of CNT n-doping state changes by varying the amount of NADH, the amount of the NADH solution is adjusted in a manner that the total number of drops of the NADH solution is increased. Water is used as solvent. The concentration of the NADH solution is 1.35 mM (0.1 wt %) and the CNT-FET is the same as that of Experiment 1.

Figure 3:
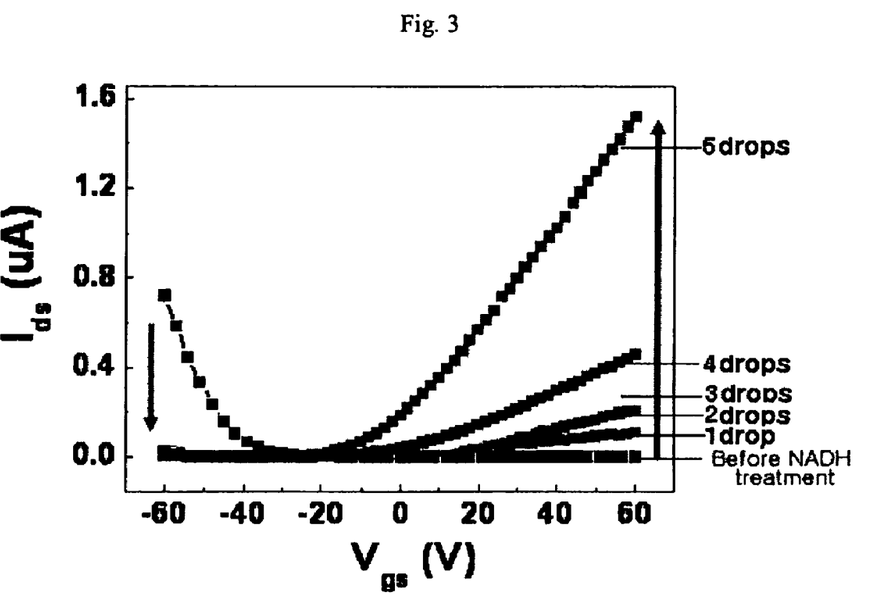
FIG. 3 is an $I_{ds}$-$V_{gs}$ graph showing a change of n-doping state depending on an amount of NADH solution according to an exemplary embodiment, where the X axis represents $V_{gs}$ (V) and the Y axis represents $I_{ds}$ (μA)

FIG. 3 is an $I_{ds}$-$V_{gs}$ graph showing a change of n-doping state depending on an amount of NADH solution in this experiment. In FIG. 3, the unit of the drain current is μA ($10^{-6}$ A).

Referring to FIG. 3, when the amount of the NADH solution increases (from one drop to five drops), the n-doping state proceeds furthermore, as may be seen from the decreased hole current and increased electron current. Therefore, it can be said that the extent of n-doping may be adjusted by controlling the amount of the NADH solution. This means that CNT n-doping controllability may be obtained when using NADH.

Experiment 3

Experiment on Change of CNT n-doping State Depending on the Concentration of NADH Solution In order to evaluate the change of CNT n-doping state depending on the concentrations of NADH solution, two NADH solutions with different NADH concentrations of 1 wt % (13.5 mM) and 10 wt % (135 mM) respectively are prepared. Water is used as solvent. The CNT-FET is the same as that of Experiment 1. One drop from each NADH solutions is introduced on the CNT channel.

Figure 4:
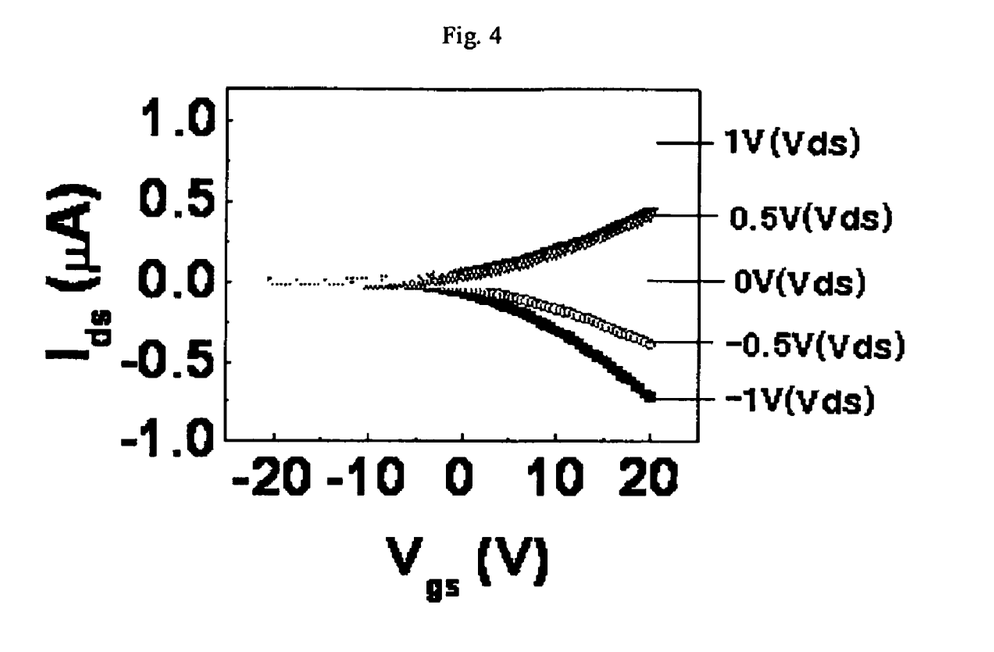
FIGS. 4 and 5 are $I_{ds}$-$V_{gs}$ graphs showing n-doping state changes depending on concentration of NADH solutions according to exemplary embodiments, where the X axis represents $V_{gs}$ (V) and the Y axis represents $I_{ds}$ (μA) in FIG. 4 and the X axis represents $V_{gs}$ (V) and the Y axis represents $I_{ds}$ (nA) in FIG. 5.
Figure 5:
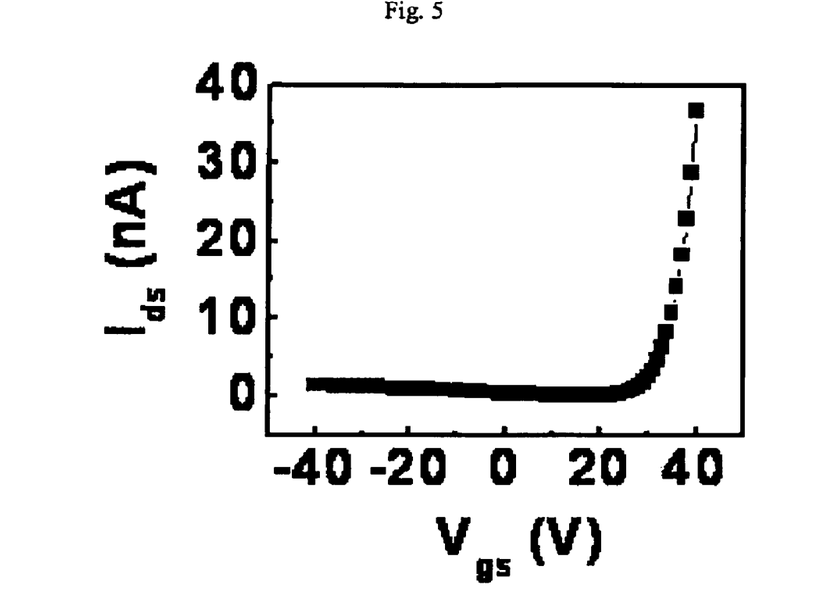

FIGS. 4 and 5 are respectively $I_{ds}$-$V_{gs}$ graphs showing changes of n-doping states depending on the concentrations of NADH solutions in this experiment. In FIG. 4, the unit of the drain current is μA ($10^{-6}$ A), and, in FIG. 5, the unit of the drain current is nA ($10^{-9}$ A). Further, FIG. 4 shows the n-doping effect when the drain voltage ($V_{ds}$) is varied.

Referring to FIG. 4, n-doping effect is seen when using NADH solution (1 wt %). Herein, the n-doping effect is seen for all the drain voltages such as about 1 V, about 0.5 V, about 0 V, about −0.5 V and about −1 V.

Referring to FIG. 5, n-doping proceeds to a greater extent when using he NADH solution with a concentration of 10 wt %.

Accordingly, it can be said that the n-doping state may also be adjusted by controlling the concentration of NADH solution. This means that CNT n-doping controllability may be obtained when using NADH.

Experiment 4

Experiment on Doping Stability

Stability of CNT n-doping state depending on time is evaluated. The concentration of the NADH solution (solvent: water) is 13.5 mM (1 wt %) and the CNT-FET is the same as that of Experiment 1.

Figure 6:
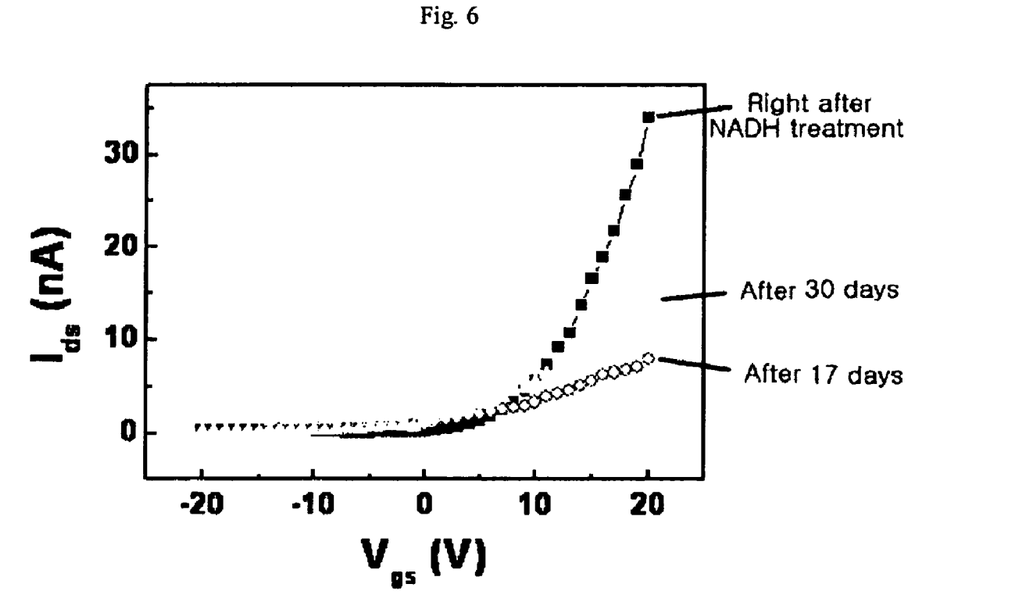
FIG. 6 is an $I_{ds}$-$V_{gs}$ graph showing an n-doping stability in the air after NADH solution treatment according to an exemplary embodiment, where the X axis represents $V_{gs}$ (V) and the Y axis represents $I_{ds}$ (nA)

FIG. 6 is an $I_{ds}$-$V_{gs}$ graph showing the doping stability in the air in three cases of right after the NADH solution treatment, after 17 days from the NADH solution treatment and after 30 days from the NADH solution treatment (respectively referred to "right after NADH treatment", "after 17 days" and "after 30 days"). In FIG. 6, the unit of the drain current is nA ($10^{-9}$ A).

As seen in FIG. 6, although the current level is decreased to some extent after 17 days and after 30 days, the n-type characteristics are still maintained in the two cases. Additionally, the current level increases after 30 days compared to after 17 days. This means that CNT n-doping stability over a long period of time may be obtained when using NADH.

Experiment 5

Experiment on CNT n-doping Effect by Nicotinamide

In order to evaluate the CNT n-doping effect by nicotinamide, the following experiment is performed. First, nicotinamide (nicotinamide 99+%; commercially available at Aldrich Chemical Co. Milwaukee Wis. USA) solution is prepared. Water is used as solvent. The concentration of the nicotinamide solution is set as 13.5 mM. The CNT-FET is the same as that of Experiment 1.

Figure 7A:
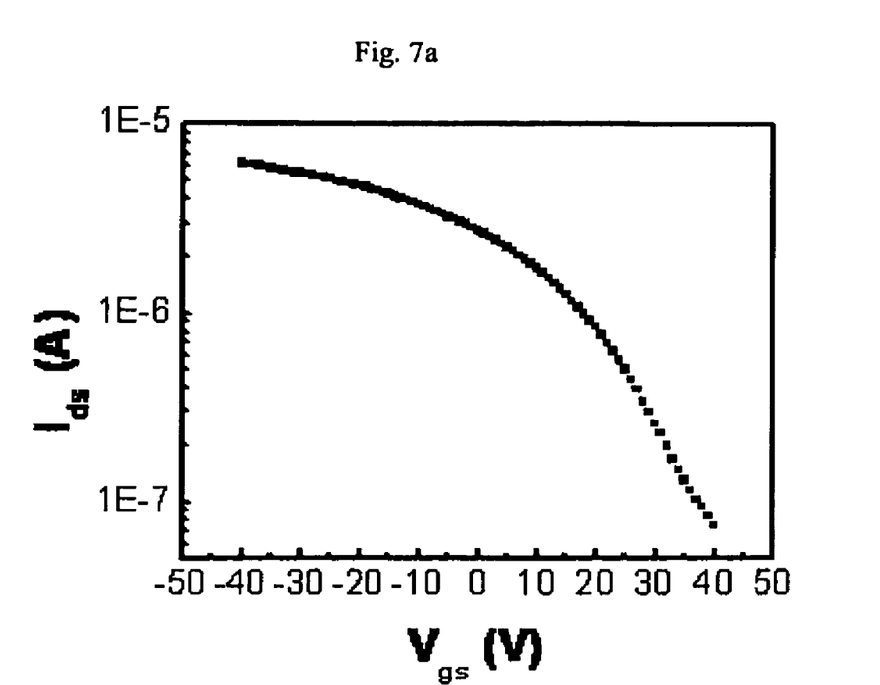
Figure 7B:
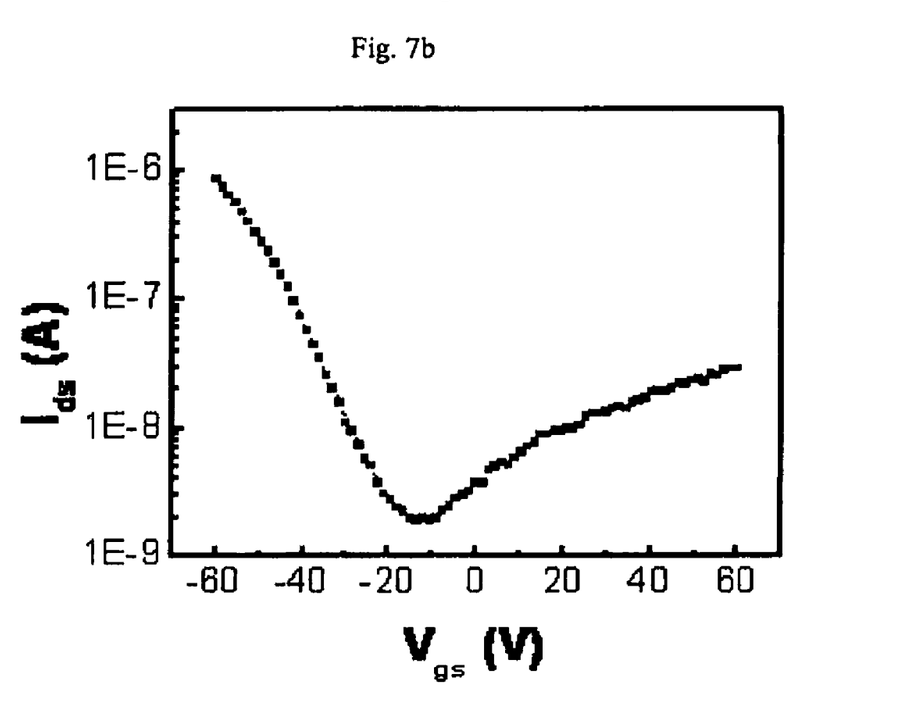

FIG. 7 is an $I_{ds}$-$V_{gs}$ graph showing the n-doping effect when using nicotinamide in this experiment. FIG. 7a represents before dropping the nicotinamide solution, and FIG. 7b represents after dropping the nicotinamide solution.

As in the experiments where the NADH solution is used, the initial p-doping state of CNT is changed into n-doping state after dropping the nicotinamide solution, which shows that the CNT n-doping effect by NADH is due to the presence of the nicotinamide in NADH.

Experiment 6

Application to p-n Junction Diode

The CNT n-doping capability of NADH is applied to a p-n junction diode using CNT. The NADH solution is the same as that of Experiment 1.

Figure 8:
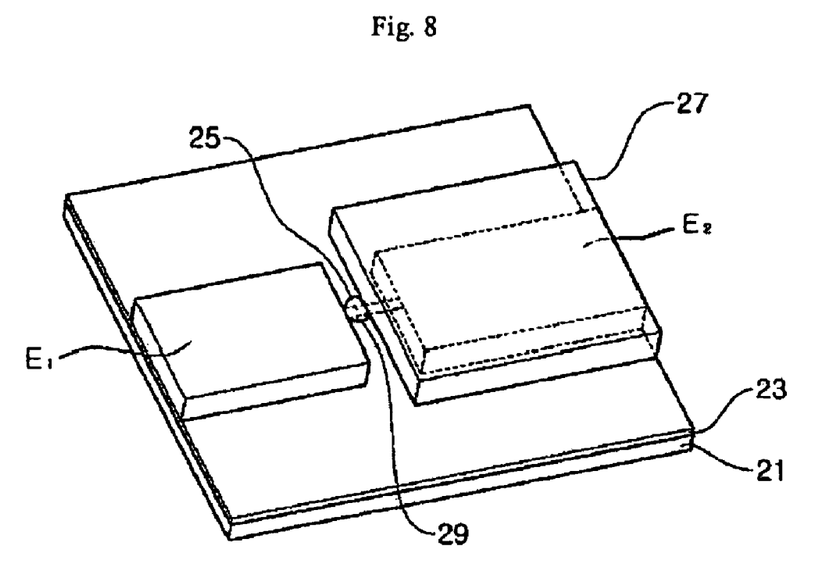
FIG. 8 is a schematic view of p-n junction diode according to an exemplary embodiment.

FIG. 8 is a schematic view of a p-n junction diode in this experiment.

Referring to FIG. 8, an SiO$_2$ insulating layer (23) is formed on an Si substrate (21), and Cr and Au electrodes E1, E2 are formed thereupon. A CNT channel (25) is formed between the electrodes. A photoresist layer (27) is used to passivate half of the CNT channel. One drop of NADH solution (100 µL) (29) is introduced on the remaining portion of the CNT channel using a micropipette, and then heated at about 150° C. for about 3 minutes.

Figure 9A:
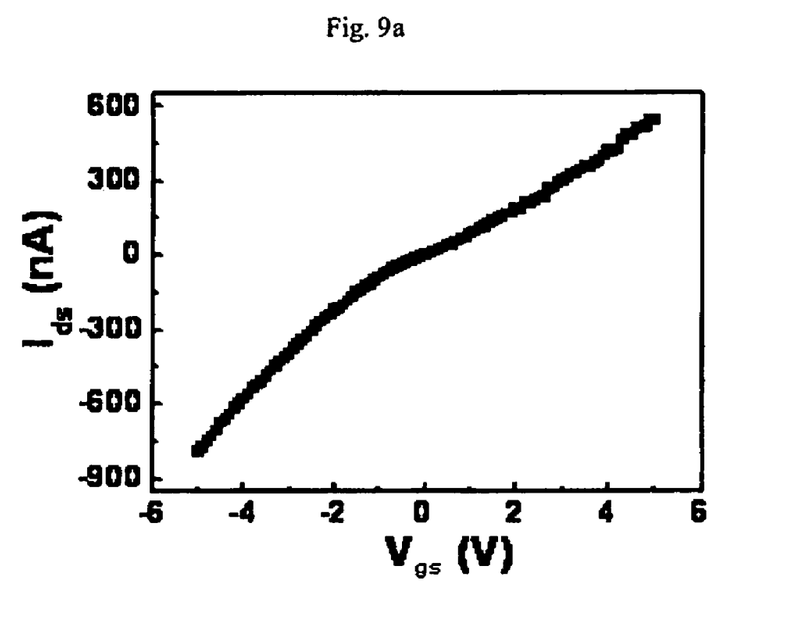
Figure 9B:
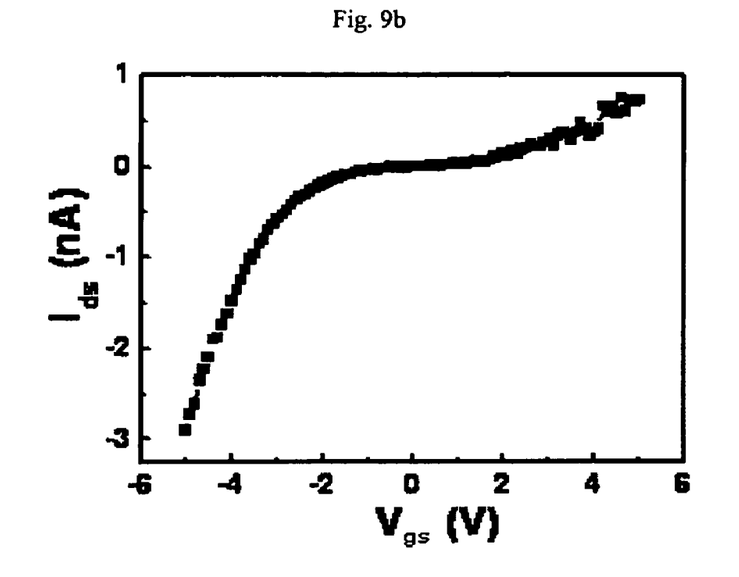

FIG. 9 is an $I_{ds}$-$V_{gs}$ graph of the p-n junction diode in FIG. 8. FIG. 9a represents before the NADH solution treatment, and FIG. 9b represents after NADH solution treatment. In FIG. 9, the unit of the drain current is nA ($10^{-9}$ A). Referring to FIG. 9, the characteristics of a p-n junction diode is seen after NADH solution treatment.

Experiment 7

Application to CMOS

The CNT n-doping capability of NADH is applied to a CMOS using CNT. The NADH solution is the same as that of Experiment 1.

Figure 10:
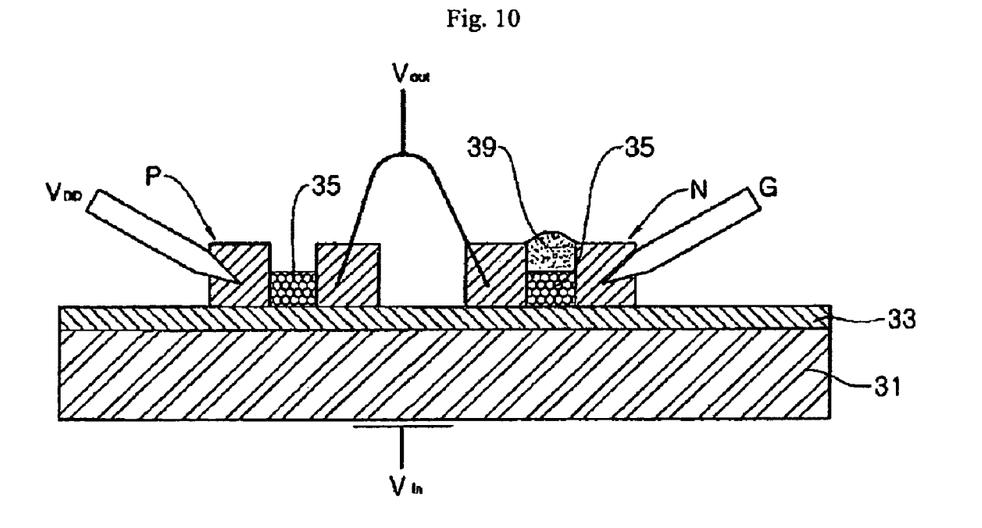
FIG. 10 is a schematic view of CMOS according to an exemplary embodiment.

FIG. 10 is a schematic view of a CMOS in this experiment.

In FIG. 10, a back gate (31), an SiO$_2$ insulating layer (33), a p-type transistor P and an n-type transistor N are schematically illustrated. CNT channels (35) are formed between electrodes at the p-type transistor P and the n-type transistor N. A voltage input terminal $V_{in}$ is connected to the back gate (31), and a voltage output terminal $V_{out}$ is connected to the transistors P, N. The n-type transistor N is earthed to ground G, and a source voltage $V_{DD}$ of 2 V is output from the p-type transistor P.

One drop of the NADH solution (100 µL) (39) is introduced on the n-type transistor N using a micropipette, and heated at about 150° C. for about 3 minutes.

Figure 11A:
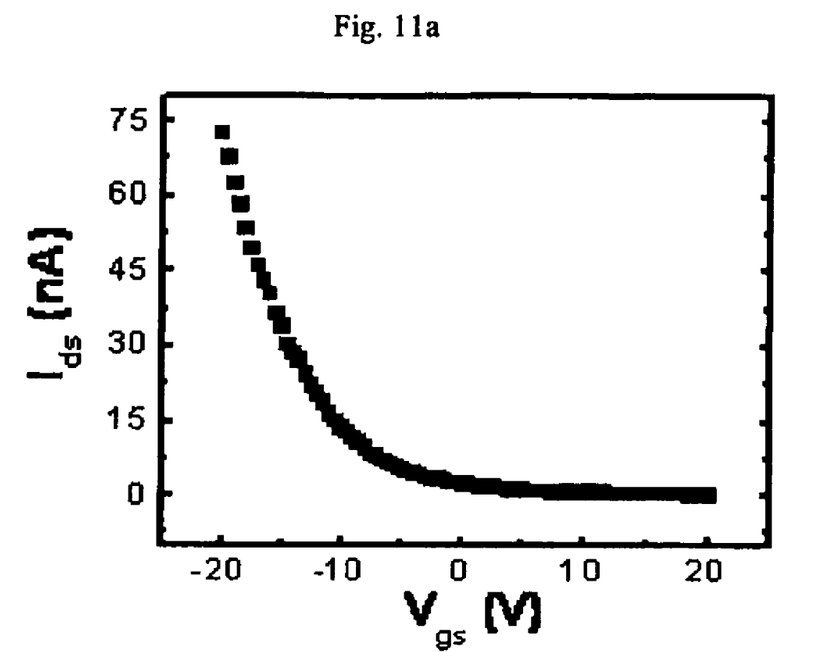
Figure 11B:
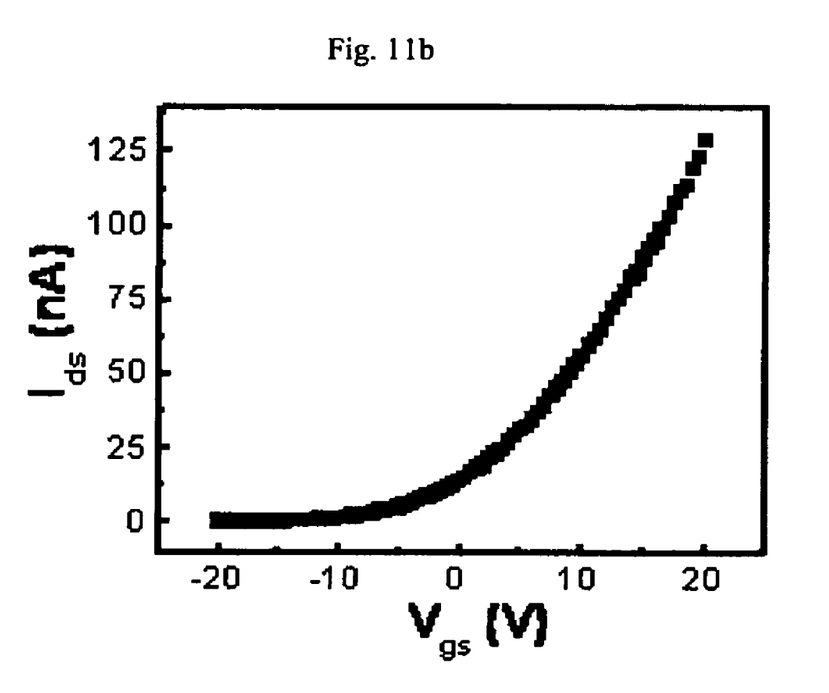
Figure 11C:
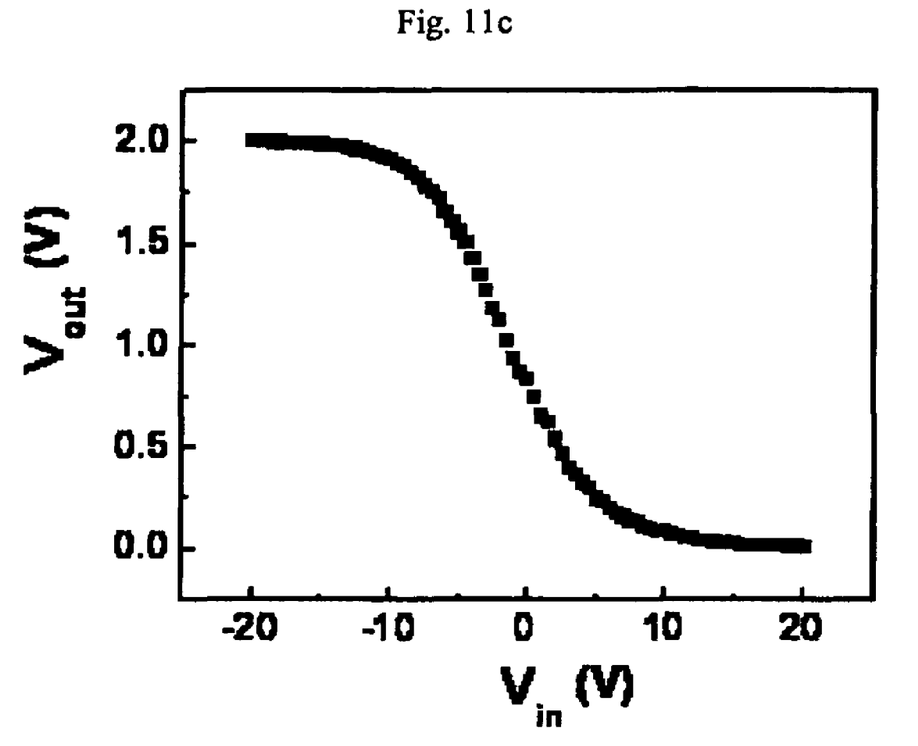

FIG. 11 is a graph showing the characteristics of the CMOS in FIG. 10. FIG. 11a is an $I_{ds}$-$V_{gs}$ graph of the p-type transistor, FIG. 11b is an $I_{ds}$-$V_{gs}$ graph of the n-type transistor N, and FIG. 11c is a $V_{in}$-$V_{out}$ graph of the CMOS. In FIGS. 11a and 11b, the unit of the drain current is nA ($10^{-9}$ A).

Referring to FIG. 11, the characteristics of CMOS are seen after NADH solution treatment.

While the invention has been shown and described with reference to certain exemplary embodiments thereof, it will be understood by those skilled in the art that various changes in form and details may be made thereto without departing from the spirit and scope of the invention as defined by the appended claims.

In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A carbon nano-tube (CNT) n-doping composition comprising:
    carbon nano-tubes and a material which n-dopes a carbon nano-tube, said n-doping material comprising nicotinamide and a compound which is chemically combined with nicotinamide,
    wherein the compound which is chemically combined with nicotinamide is at least one selected from the group consisting of nicotinamide mononucleotide (NMN), a nicotinamide adenine dinucleotide (NAD), a nicotinamide adenine dinucleotide phosphate (NADP), reduced nicotinamide mononucleotide (NMNH), a reduced nicotinamide adenine dinucleotide (NADH) and a reduced nicotinamide adenine dinucleotide phosphate (NADPH).

2. The CNT n-doping composition according to claim 1, wherein according to claim 1 nicotinamide or the compound which is chemically combined with nicotinamide is in its reduced form.

3. The CNT n-doping composition according to claim 1, wherein the CNT n-doping material further compromises a solvent in which the CNT n-doping material is dissolved.

4. A CNT n-doping method comprising:
n-doping a CNT with a material comprising nicotinamide and a compound which is chemically combined with nicotinamide,
wherein the compound which is chemically combined with nicotinamide is at least one selected from the group consisting of nicotinamide mononucleotide (NMN), a nicotinamide adenine dinucleotide (NAD), a nicotinamide adenine dinucleotide phosphate (NADP), reduced nicotinamide mononucleotide (NMNH), a reduced nicotinamide adenine dinucleotide (NADH) and a reduced nicotinamide adenine dinucleotide phosphate (NADPH).

5. The CNT n-doping method according to claim 4, further comprising:
heating the CNT to which the material is provided.

6. The CNT n-doping method according to claim 4, wherein the n-doping state of the CNT is adjusted by controlling the amount of the material.

7. The CNT n-doping method according to claim 4, wherein the material is mixed with a solvent to prepare a solution and the solution is provided to the CNT.

8. The CNT n-doping method according to claim 7, wherein the n-doping state of the CNT is adjusted by controlling the amount of the solution.

9. The CNT n-doping method according to claim 7, wherein the n-doping state of the CNT is adjusted by controlling the concentration of the material in the solution.

10. The CNT n-doping method according to claim 5, wherein the n-doping state of the CNT is adjusted by controlling at least one variable selected from the group consisting of heating temperature and heating time.

11. The CNT n-doping method according to claim 10, wherein the heating temperature is about 40° C. to about 250° C.

12. The CNT n-doping method according to claim 10, wherein the heating time is about 10 seconds to about 100 hours.

13. The CNT n-doping method according to claim 5, wherein the material is sublimed to be provided to the CNT.

14. A carbon nano-tube (CNT) n-doped with a material comprising nicotinamide and a compound which is chemically combined with nicotinamide,
wherein the compound which is chemically combined with nicotinamide is at least one selected from the group consisting of nicotinamide mononucleotide (NMN), a nicotinamide adenine dinucleotide (NAD), a nicotinamide adenine dinucleotide phosphate (NADP), reduced nicotinamide mononucleotide (NMNH), a reduced nicotinamide adenine dinucleotide (NADH) and a reduced nicotinamide adenine dinucleotide phosphate (NADPH).

15. The CNT according to claim 14, wherein the CNT exhibits n-type characteristics in the air.

16. The CNT according to claim 14, wherein the CNT exhibits n-type characteristics in the air after 30 days from being n-doped.

17. A device comprising a carbon nano-tube (CNT) n-doped with a material comprising nicotinamide and a compound which is chemically combined with nicotinamide,
wherein the compound which is chemically combined with nicotinamide is at least one selected from the group consisting of nicotinamide mononucleotide (NMN), a nicotinamide adenine dinucleotide (NAD), a nicotinamide adenine dinucleotide phosphate (NADP), reduced nicotinamide mononucleotide (NMNH), a reduced nicotinamide adenine dinucleotide (NADH) and a reduced nicotinamide adenine dinucleotide phosphate (NADPH).

18. The device according to claim 17, wherein the device is a field-effect transistor.

19. The device according to claim 17, wherein the device is a p-n junction diode.

20. The device according to claim 17, wherein the device is a complementary metal oxide semiconductor (CMOS).

* * * * *